US00PP28520P3

(12) United States Plant Patent
Bean

(10) Patent No.: US PP28,520 P3
(45) Date of Patent: Oct. 10, 2017

(54) ***AGAPANTHUS* HYBRID PLANT NAMED 'AMPU001'**

(50) Latin Name: ***Agapanthus* hybrid**
Varietal Denomination: AMPU001

(71) Applicant: Quinton Bean, Johannesburg (ZA)

(72) Inventor: Quinton Bean, Johannesburg (ZA)

( * ) Notice: Subject to any disclaimer, the term of this patent is extended or adjusted under 35 U.S.C. 154(b) by 153 days.

(21) Appl. No.: 14/756,366

(22) Filed: Sep. 2, 2015

(65) Prior Publication Data

US 2016/0081254 P1 Mar. 17, 2016

Related U.S. Application Data

(60) Provisional application No. 62/049,009, filed on Sep. 11, 2014.

(51) Int. Cl.
*A01H 5/02* (2006.01)

(52) U.S. Cl.
USPC ..... Plt./398

(58) Field of Classification Search
USPC ..... Plt./398
CPC ..... A01H 5/0272
See application file for complete search history.

*Primary Examiner* — Kent L Bell
(74) *Attorney, Agent, or Firm* — Samuel R. McCoy, Jr.

(57) ABSTRACT

A new cultivar of *Agapanthus*, 'AMPU001', that is characterized by its fast growing and fast multiplying growth habit, a compact plant habit, inflorescences that form dense umbels of flowers that are dark violet-purple in color, an extended flowering season blooming and re-blooming from early spring to late summer and sporadically in early fall, a very floriferous blooming period producing an unusually high number of inflorescences, and its good resistance to fungal infection from *Macrophoma agapanthii.*

2 Drawing Sheets

Latin name of the genus and species: The Latin name of the novel variety disclosed herein is *Agapanthus* hybrid 'AMPU001'.

Variety denomination: The inventive variety of *Agapanthus* hybrid disclosed herein has been given the variety denomination 'AMPU001'.

BACKGROUND OF THE INVENTION

The present invention relates to a new and distinct variety of *Agapanthus* hybrid, which has been named 'AMPU001'. *Agapanthus*, commonly called "lily of the Nile", is a flowering perennial native to South Africa that forms clumps of dark green strap-like leaves. In spring, umbels rise above the foliage which bear numerous flowers in colors ranging from pale violet to dark purple. Its consistent size and performance, combined with its attractive inflorescences through its hardiness range make it an ideal choice for specimen, borders and mass plantings in any full to filtered sun to shady, low-maintenance landscape or container.

Parentage: The cultivar 'AMPU001' is a seedling selection resulting from a controlled pollination breeding program by the Inventor in Hartebeespoort, Northwest Province, South Africa. The objective of the breeding program is to develop new cultivars of *Agapanthus* that are fast growing, early flowering and that display repeat flowering and unique flower colors. The Inventor made a controlled cross in October of 2007 between an unnamed plant of *Agapanthus caulescens* hybrid from the Inventor's breeding program as the female parent and an unnamed plant of *Agapanthus campanulatus* hybrid from the Inventor's breeding program as the male parent. The Inventor selected 'AMPU001' in November of 2009 as a single unique plant amongst the seedlings that resulted from the above cross.

Asexual Reproduction: Asexual propagation of the new cultivar was first accomplished by division by the Inventor in Hartebeespoort, Northwest Province, South Africa in February of 2010. Asexual propagation by division and tissue culture has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'AMPU001' as a distinct cultivar of *Agapanthus.*

1. 'AMPU001' exhibits a fast growing and fast multiplying growth habit.
2. 'AMPU001' exhibits a compact plant habit.
3. 'AMPU001' exhibits inflorescences that form dense umbels of flowers that are violet-purple in color.
4. 'AMPU001' exhibits an extended flowering season blooming and re-blooming from early spring to late summer and sporadically in early fall.
5. 'AMPU001' exhibits a very floriferous blooming period producing an unusually high number of inflorescences.
6. 'AMPU001' exhibits good resistance to fungal infection from *Macrophoma agapanthii.*

DETAILED BOTANICAL DESCRIPTION OF THE VARIETY

Figure 1:
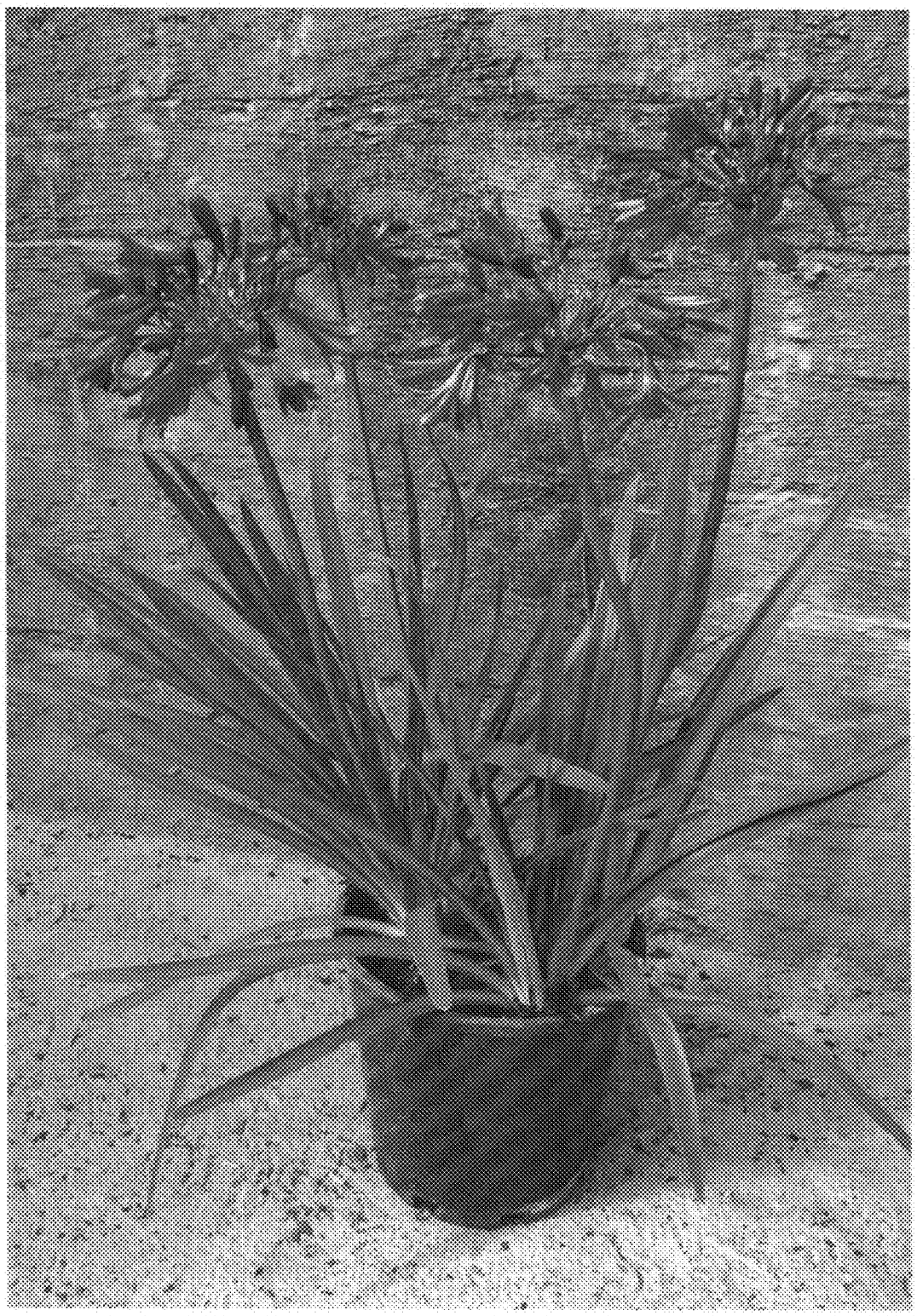
FIG. 1 shows as true as is reasonably possible to obtain in color photographs of this type, an exemplary 'AMPU001' specimen, approximately 12 months of age, grown at a wholesale nursery in Hartebeespoort, Northwest Province, South Africa.
Figure 2:
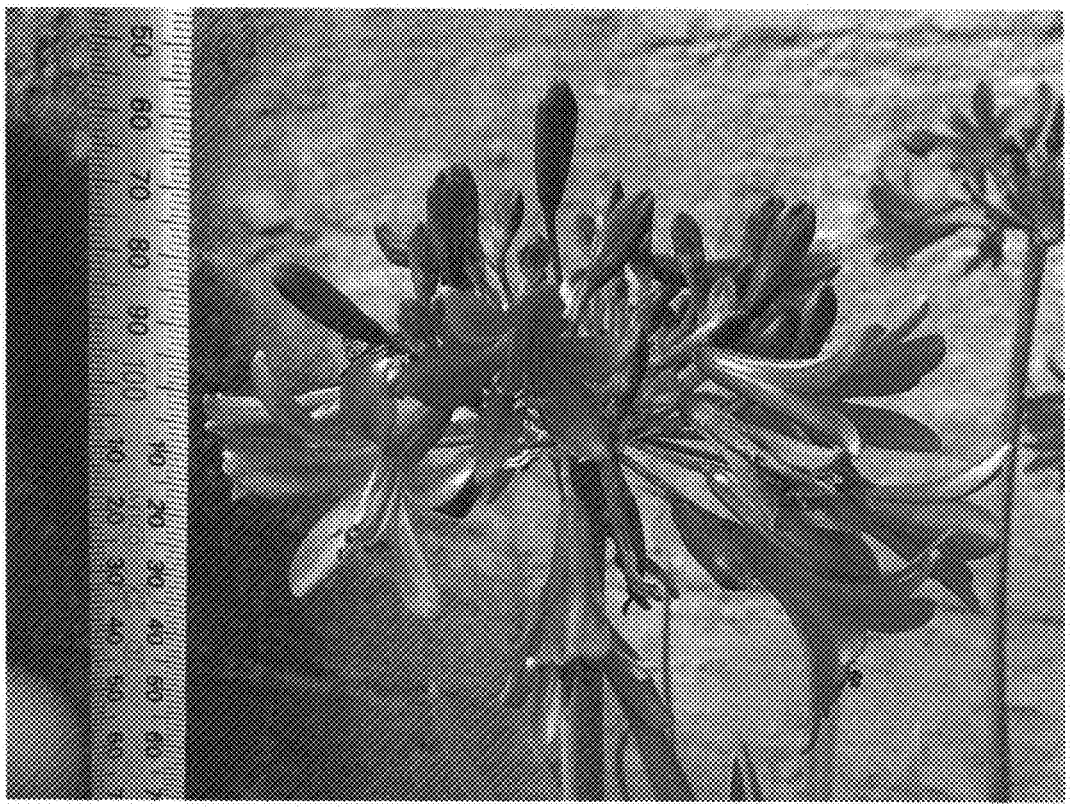
FIG. 2 shows as true as is reasonably possible to obtain in color photographs of this type, an exemplary umbel of 'AMPU001'.

The following is a detailed botanical description of a new and distinct *Agapanthus* hybrid seedling selection known as 'AMPU001'. Unless indicated otherwise, the descriptions disclosed herein are based upon observations made in May 2014 of mature 'AMPU001' plants, approximately 12 months of age, grown at a wholesale nursery facility in Hartebeespoort, Northwest Province, South Africa. Plants were grown in full sun; fertilized with slow release granular fertilizer and regularly watered with overhead irrigation. No pest or disease measures were taken during production.

Those skilled in the art will appreciate that certain characteristics will vary with older or, conversely, with younger plants. 'AMPU001' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 1986 edition. Note that generic color descriptions such as "green" do not exist in The R.H.S. charts and the corresponding R.H.S. colors are quoted.

The distinguishing features and other characteristics of *Agapanthus* hybrid 'AMPU001' are apparent from the description provided below.

General plant description:

- *Plant habit*.—Rhizomatous herbaceous perennial with an arching habit.
- *Height*.—30 cm to the tallest leaf, as measured; 46 cm to the top of the floral plane.
- *Width*.—30 cm, as measured.
- *Bloom period*.—AMPU001 exhibits an extended flowering season, blooming and re-blooming from early spring to late summer and sporadically in early fall.
- *Hardiness*.—USDA Zone 9 to 10.
- *Environmental tolerances*.—Prefers to be grown in full sun. Drought tolerant once established; moderate to good recovery with watering after severe wilting. Tolerates a wide range of soil types from sandy loam to loamy clay.
- *Pest and disease susceptibility or resistance*.—'AMPU001' exhibits good resistance to fungal infection from *Macrophoma agapanthii*.
- *Propagation*.—Propagation is accomplished through division of rhizomes.
- *Time to initiate roots*.—Approximately 3 weeks.
- *Crop time*.—Depending on latitude of and microclimate of growing location, a fully rooted cutting requires approximately 3 months with an additional 5 to 7 months needed to produce a mature and marketable 15 cm container.

Roots: The roots are fibrous and freely-branched, colored white, fleshy, similar to other *Agapanthus*; high root density.

Stem:

- *Branching habit*.—Acaulescent, rhizomatous plant with shoots emerging from rhizomes with an upright attitude.

Basal shoots:

- *Shoots density*.—6 divisions, or propagules, per one square foot area, with the oldest propagules near the center of the plant's crown possessing 12 to 14 leaves and shoots of varying ages and sizes.
- *Shoot strength*.—Medium.
- *Cross section*.—Concave.
- *Shoot color* (*adaxial & abaxial surfaces*).—Yellow-green RHS 144A.
- *Shoot surface texture*.—Smooth.

Foliage:

- *Type*.—Evergreen.
- *Arrangement*.—Basal.
- *Division*.—Simple.
- *Attitude*.—Arched.
- *Shape*.—Linear.
- *Apex*.—Acute.
- *Base*.—Sheathed.
- *Cross section*.—Flat.
- *Venation*.—Parallel.
- *Vein color* (*adaxial surfaces*).—Same as surrounding foliage.
- *Vein color* (*abaxial surfaces*).—Same as surrounding foliage.
- *Margins*.—Entire.
- *Attachment*.—Acaulescent.
- *Texture*.—Smooth and glossy.
- *Surface hairiness* (*adaxial surface*).—Glabrous.
- *Surfaces hairiness* (*abaxial surface*).—Glabrous.
- *Mature leaf dimensions*.—Longest observed leaf measuring length 310 mm, average width 28 mm at widest point.
- *Mature leaf color* (*adaxial & abaxial surface*).—Green RHS 143B and Yellow-green RHS 144A, respectively.
- *Petiole*.—Leaves are acaulescent; sessile.
- *Stipules*.—Absent.

Inflorescence:

- *Inflorescence type*.—Umbellate.
- *Umbel diameter*.—Largest observed is 130 mm wide.
- *Umbel depth*.—Largest observed is 50 to 60 mm deep.
- *Number of umbels per pot*.—Potentially more than one inflorescence per propagule, per growing season.
- *Number of flowers per umbel*.—More than 55 flowers and buds may be present at any given time.
- *Scape dimensions*.—Largest observed measuring at 375 mm tall and 8 mm wide at the base, as measured.
- *Other characteristics of scape*.—Color is Green RHS 143B; cylindrical shape; texture is smooth; glabrous.

Buds:

- *Bud shape*.—Obelliptic; apex round; base cuneate.
- *Bud dimensions*.—34 mm long and 8 mm wide, prior to anthesis.
- *Bud color*.—Purple RHS 79B.
- *Bud texture*.—Glabrous.

Flowers:

- *General*.—Apetalous flowers; shape is campanulate; self-cleaning and non-fragrant. Attitude is upward and outward.
- *Lastingness*.—Approximately 7 days.

*Pedicel dimensions.*—18 mm long and 1.5 mm wide, as measured.
*Pedicel color.*—Green RHS 143B.
*Pedicel surface.*—Glabrous.
*Perianth dimensions.*—Approximately 42 mm in diameter and 32 mm deep, at anthesis.
*Tepals.*—Six basally fused tepals.
*Tepal shape.*—Oblanceolate; apex is round.
*Tepal dimensions.*—34 mm long and 13 mm wide, as measured.
*Outer tepal color.*—Purple RHS 79D, yet appearing as Violet RHS 82A under high light exposure.
*Inner tepal color.*—Violet RHS 82A at and near the midrib, with purple RHS 77D in areas between margins and midrib.
*Tepal surface.*—Smooth; glabrous.
*Tepal margin.*—Entire.

Reproductive organs:
*Stamens.*—Six.
*Stamen attachment.*—Each is adnate to a corresponding tepal.
*Filament color.*—Purple RHS 77D at base, becoming Purple RHS 79D near apex.
*Filament dimensions.*—20 mm long and less than 1 mm wide.
*Anther attachment.*—Versatile.
*Anther dimensions.*—1.5 to 2 mm long and 1 to 1.5 mm wide.
*Anther color.*—Appearing as a mixture of Black RHS 202A and Green-yellow RHS 1B.
*Pollen.*—Present; high quantity; color appears to be Green-Yellow RHS 1B.
*Pistil.*—One.
*Pistil dimensions.*—18 mm long, from apex of ovary; width is less than 1 mm.
*Pistil color.*—Purple RHS 77D at base, becoming Purple RHS 79D near apex.
*Style length.*—1.7 cm.
*Style color.*—Purple RHS 77D and becoming Purple RHS 79D towards the distal end.
*Stigma shape.*—Capitate.
*Stigma length.*—0.075 cm.
*Stigma diameter.*—0.075 cm.
*Stigma color.*—Purple RHS 79D.
*Ovary shape.*—Oblong.
*Ovary color.*—Yellow-Green RHS 150B.
*Ovary dimensions.*—7.5 mm long and 2.5 mm wide.
*Ovary position.*—Superior.

Fruit and seeds: Not observed.

COMPARISONS WITH THE PARENTS

The female parent of 'AMPU001' differs from 'AMPU001' in having a shorter flowering season, in having few flowers per inflorescence, and in producing fewer inflorescences.

The male parent of 'AMPU001' differs from 'AMPU001' in being slower growing, in having a shorter flowering season, in being more susceptible to disease, and in having flowers that are dark blue in color.

COMPARISONS WITH SIMILAR *AGAPANTHUS* HYBRID CULTIVARS KNOWN TO THE INVENTOR

'AMPU001' can be most closely compared to the *Agapanthus* cultivars 'Benfran' (U.S. Plant Pat. No. 21,705) and 'ATIBlu' (U.S. Plant Pat. No. 14,332). 'Benfran' is similar to 'AMPU001' in having a compact plant habit and in being fast to multiply. 'Benfran' differs from 'AMPU001' in being less cold tolerant, in having flowers that are light blue in color, in having fewer inflorescences, and in exhibiting very little to no re-blooming. 'ATIBlu' is similar to 'AMPU001' in being a prolific producer of inflorescences and in exhibiting good cold tolerance 'ATIBlu' differs from 'AMPU001' in having flowers that are pale blue in color, in having a shorter flowering season, in exhibiting less re-blooming, in having flowering stems that are taller in height, and in having leaves that are narrower.

That which is claimed is:

1. A new and distinct *Agapanthus* hybrid plant named 'AMPU001', substantially as described and illustrated herein.

* * * * *